United States Patent [19]

Smith

[11] Patent Number: 5,196,436

[45] Date of Patent: Mar. 23, 1993

[54] DEXTROMETHORPHAN ANTITUSSIVE COMPOSITIONS

[75] Inventor: Ronald L. Smith, West Chester, Ohio

[73] Assignee: The Procter & Gamble Company, Cincinnati, Ohio

[21] Appl. No.: 841,244

[22] Filed: Feb. 24, 1992

Related U.S. Application Data

[63] Continuation of Ser. No. 606,294, Oct. 31, 1990, abandoned.

[51] Int. Cl.$^5$ .............................................. A61K 31/44
[52] U.S. Cl. ....................................................... 514/289
[58] Field of Search ............................................ 514/289

[56] References Cited

U.S. PATENT DOCUMENTS

| | | | |
|---|---|---|---|
| 4,427,681 | 1/1984 | Munshi | 424/260 |
| 4,454,140 | 6/1984 | Goldberg et al. | 424/260 |
| 4,892,877 | 1/1990 | Sorrentino | 514/289 |

OTHER PUBLICATIONS

Chem. Abstr-100 109144J (1984).
Chem. Abst.-106-72813k (1987).
Merck Index, 10th Edition (1983), M. Windholz ed., No. 8009, p. 1170.
Physician's Desk Reference for Nonprescription Drugs, 11th Edition (1990), E. R. Barnhardt, pub., p. 306.
Physician's Desk Reference, 44th Edition (1990), E. R. Barnhardt, publ. p. 309.
Beckett, A. H. and E. G. Triggs, "Buccal Absorption of Basic Drugs and Its Application as an In Vivo Model of Passive Drug Transfer Through Lipid Membranes", Journal of Pharmaceutics and Pharmacology, vol. 19 Supplement (1967), pp. 31S–41S.

*Primary Examiner*—S. J. Friedman
*Attorney, Agent, or Firm*—M. B. Graff, IV; J. J. Yetter; T. H. O'Flaherty

[57] ABSTRACT

The subject invention involves antitussive pharmaceutical compositions for the peroral administration of dextromethorphan, the composition being at a pH of from about 8 to about 11.

8 Claims, No Drawings

DEXTROMETHORPHAN ANTITUSSIVE COMPOSITIONS

This is a continuation of application Ser. No. 07/606,294, filed on Oct. 31, 1990, now abandoned.

TECHNICAL FIELD

This invention is concerned with novel antitussive compositions containing dextromethorphan. More particularly, it is concerned with compositions and methods for rapidly achieving therapeutic systemic levels of dextromethorphan.

BACKGROUND OF THE INVENTION

Dextromethorphan (racemethorphan), 3-methoxy-17-methylmorphinan, is disclosed in the Merck Index. 10th edition (1983), M. Windholz, ed., No. 8009, p. 1170; it is disclosed to be an antitussive agent.

Dextromethorphan hydrobromide is used extensively as an antitussive agent in commercial products as disclosed in the *Physician's Desk Reference for Nonprescription Drugs*, 11th Edition (1990), E. R. Barnhardt, pub., p. 306, and in *Physician's Desk Reference*, 44th Edition (1990), E. R. Barnhardt, pub., p. 309: Bayer Children's Cough Syrup by Glenbrook, Benylin DM by Parke-Davis, Benylin Expectorant by Parke-Davis, Cerose-DM by Wyeth-Ayerst, Cheracol D Cough Formula by Upjohn, Cheracol Plus Head Cough/Cold Formula by Upjohn, Cough Formula Comtrex by Bristol-Myers Products, Comtrex Multi-Symptom Cold Reliever Tablets/Caplets/Liquid/Liquigels by Bristol-Myers Products, Contac Cough Formula by SmithKline Consumer, Contac Cough & Sore Throat Formula by SmithKiline Consumer, Contac Jr. Children's Cold Medicine by SmithKline Consumer, Contac Nighttime Cold Medicine by SmithKline Consumer, Contac Severe Cold Formula Caplets by SmithKline Consumer, Dimacol Caplets by Robins, Dorcol Children's Cough Syrup by Sandoz Consumer, Hold by SmithKline Beecham, Naldecon DX Adult Liquid by Bristol Laboratories, Naldecon DX Children's Syrup by Bristol Laboratories, Naldecon DX Pediatric Drops by Bristol Laboratories, Naldecon Senior DX Cough/Cold Liquid by Bristol Laboratories, Novahistine DMX by Lakeside Pharmaceuticals, Pediacare Cough-Cold Formula Liquid and Chewable Tablets by McNeil Consumer Products, Pediacare Night Rest Cough-Cold Formula Liquid by McNeil Consumer Products, Robitussin Night Relief by Robins, Robitussin-CF by Robins, Robitussin-DM by Robins, Scot-Tussin Sugar-Free DM Cough & Cold Medicine by Scot-Tussin, Snaplets-DM by Baker Cummins Pharmaceuticals, Snaplets-Multi by Baker Cummins Pharmaceuticals, St. Joseph Cough Suppressant for Children by Plough, St. Joseph Nighttime Cold Medicine by Plough, Sucrets Cough Control Formula by SmithKline Beecham, Sudafed Cough Syrup by Burroughs Wellcome, Triaminic Night Light by Sandoz Consumer, Triaminic-DM Syrup by Sandoz Consumer, Triaminicol Multi-Symptom Cold Tablets by Sandoz Consumer, Triaminicol Multi-Symptom Relief by Sandoz Consumer, Tylenol Cold Medication Caplets and Tablets by McNeil Consumer Products, Tylenol Cold Medication Liquid by McNeil Consumer Products, Tylenol Cold Medication No Drowsiness Formula Caplets by McNeil Consumer Products, Vicks Children's Cough Syrup by Richardson-Vicks, Inc., Vicks Children's NyQuil by Richardson-Vicks, Inc., Vicks Cough Silencers Cough Drops by Richardson-Vicks, Inc., Vicks Daycare Daytime Colds Medicine Caplets by Richardson-Vicks, Inc., Vicks Daycare Multi-Symptom Colds Medicine Liquid by Richardson-Vicks, Inc., Vicks Formula 44 Cough Control Discs by Richardson-Vicks, Inc., Vicks Formula 44 Cough Medicine by Richardson-Vicks, Inc., Vicks Formula 44D Decongestant Cough Medicine by Richardson-Vicks, Inc., Vicks Formula 44M Multi-Symptom Cough Medicine by Richardson-Vicks, Inc., Vicks NyQuil Nighttime Colds Medicine-Original & Cherry Flavor by Richardson-Vicks, Inc., Vicks Pediatric Formula 44 Cough Medicine by Richardson-Vicks, Inc., Vicks Pediatric Formula 44 Cough & Colds Medicine by Richardson-Vicks, Inc., Vicks Pediatric Formula 44 Cough & Congestion Medicine by Richardson-Vicks, Inc., Ambenyl-D Decongestant Cough Formula by Forest Pharmaceuticals, Bromarest DX Cough Syrup by Warner Chilcott, BromFed-DM Cough Syrup by Muro, Codimal DM by Central Pharmaceuticals, Dimetane-DX Cough Syrup by Robins, Guaifenesin w/D-Methorphan Hydrobromide Syrup by Lederle, Humibid DM Tablets by Adams, IoTuss-DM Liquid by Muro, Medi-Tuss DM by Warner Chilcott, Phenergan with Dextromethorphan by Wyeth-Ayerst, Poly-Histine DM Syrup by Bock, Quelidrine Syrup by Abbott, Rondec-DM Oral Drops by Ross, Rondec DM Syrup by Ross, Tusibron-DM by RAM Laboratories, Tussar DM by Rorer Pharmaceuticals, and Tussi-Organidin DM Liquid by Wallace. Delsym Cough Suppressant Syrup by McNeil Consumer contains dextromethorphan polistirex as an antitussive agent. It is believed that all of the above commercial products containing dextromethorphan are included in compositions at about neutral pH or lower.

Beckett, A. H., & E. G. Triggs, "Buccal Absorption of Basic Drugs and Its Application as an In Vivo Model of Passive Drug Transfer Through Lipid Membranes", *Journal of Pharmaceutics and Pharmacology*, Vol. 19 Supplement (1967), pp. 31S-41S, discloses that buccal absorption of a number of drugs is substantially increased from compositions having a higher pH, when such compositions are held and circulated in the mouth for 5 minutes. Dextromethorphan is not disclosed as one of those drugs tested in *Beckett and Triggs*. The disclosure of *Beckett and Triggs* would not be expected to be very pertinent to liquid products which are generally not held in the mouth but are swallowed quickly, or even to solid products such as lozenges which are allowed to dissolve in the mouth where the dissolution liquid is rapidly swallowed.

U.S. Pat. No. 4,892,877 issued to Sorrentino on Jan. 9, 1990, discloses liquid compositions for the treatment of coughs comprising both dextromethorphan and phenol, the compositions having a pH of 5-9. U.S. Pat. No. 4,427,681 issued to Munshi on Jan. 24, 1984, discloses thixotropic compositions for the treatment of coughs comprising both dextromethorphan and Avicel ® RC-591. These patents are hereby incorporated by reference.

SUMMARY OF THE INVENTION

It is an object of the subject invention to provide dextromethorphan compositions for peroral administration which will provide more rapid antitussive action than commercially available compositions.

It is also an object of the subject invention to provide methods for achieving rapid antitussive action from dextromethorphan compositions.

The subject invention involves pharmaceutical compositions for oral administration which consist essentially of a safe and effective amount of dextromethorphan and an orally-acceptable pharmaceutical carrier, the composition having a pH of from about 8 to about 11.

The subject invention also involves pharmaceutical compositions for oral administration which comprise a safe and effective amount of dextromethorphan, safe and effective amounts of cough/cold drug actives other than phenol, and an orally-acceptable pharmaceutical carrier, the composition having a pH of from about 8 to about 11.

The subject invention also involves pharmaceutical compositions for oral administration which comprise a safe and effective amount of dextromethorphan, a safe and effective amount of phenol, and an orally-acceptable pharmaceutical carrier, the composition having a pH of from greater than 9 to about 11.

DETAILED DESCRIPTION OF THE INVENTION

The compositions and methods of the subject invention comprise a safe and effective amount of dextromethorphan, and possibly other drug actives. The phrase "safe and effective amount", as used herein, means an amount of drug active high enough to provide a significant positive modification of the condition to be treated, but low enough to avoid serious side effects (at a reasonable benefit/risk ratio), within the scope of sound medical judgment. A safe and effective amount of drug active will vary with the particular condition being treated, the age and physical condition of the patient being treated, the severity of the condition, the duration of the treatment, the nature of concurrent therapy and like factors.

Dextromethorphan is known to have pharmacological activity as an antitussive agent. As used herein, "dextromethorphan" means racemethorphan, 3-methoxy-17-methylmorphinan (dl-cis-1,3,4,9,10,10a-hexahydro-6-methoxy-11-methyl-2H-10,4a-iminoethanophenanthrene:

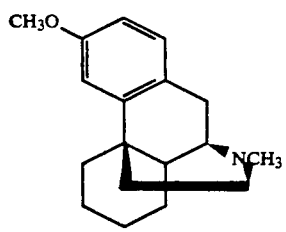

and pharmaceutically-acceptable salts thereof. Preferred salts of dextromethorphan include the hydrobromide salt.

The compositions of the subject invention preferably comprise from about 1 mg to about 50 mg dextromethorphan per dose, more preferably from about 2.5 mg to about 30 mg dextromethorphan per dose. Liquid compositions preferably comprise from about 0.02% to about 1.5% dextromethorphan, more preferably from about 0.05% to about 1% dextromethorphan, most preferably from about 0.1% to about 0.3% dextromethorphan. A typical dose for a liquid antitussive composition is from about 1 ml to about 30 ml. A dose of liquid cough syrup is more typically from about 5 ml to about 20 ml, especially about 15 ml. A dose of concentrated liquid cough spray is more typically from about 2 ml to about 5 ml, especially about 3.5 ml.

Preferred compositions of the subject invention consist essentially of a safe and effective amount of dextromethorphan, and an orally-acceptable pharmaceutical carrier, the composition having a pH of from about 8 to about 11, preferably of from about 8.4 to about 10, more preferably still of from about 8.5 to about 9.5, most preferably of about 9. Other preferred compositions of the subject invention comprise a safe and effective amount of dextromethorphan, safe and effective amounts of other cough/cold drug actives other than phenol, and an orally-acceptable pharmaceutical carrier, the composition having a pH of from about 8 to about 11, preferably from about 8.4 to about 10, more preferably still from about 8.5 to about 9.5, most preferably about 9. Other preferred compositions of the subject invention comprise a safe and effective amount of dextromethorphan, a safe and effective amount of phenol, and an orally-acceptable pharmaceutical carrier, the composition having a pH of from greater than 9 to about 11, preferably from about 9.5 to about 10, also preferably from about 9.1 to about 9.5.

It has been found that the compositions of the subject invention result in faster attainment of therapeutic blood levels of dextromethorphan, maintenance of such therapeutic blood levels for a longer time, and/or higher peak blood levels of dextromethorphan, compared to conventional lower pH dextromethorphan compositions.

The compositions of the subject invention preferably have a basic buffering strength sufficient to overcome that provided by the saliva and mucus membranes of the mouth and throat, such that the composition mixed with saliva is retained in the above pH ranges during the period that it is in the mouth and throat. Consequently, the compositions of the subject invention preferably have a basic buffer strength of at least about 0.01 milliequivalents (mEq) base per unit dose, more preferably from about 0.05 mEq to about 2.5 mEq per unit dose, most preferably from about 0.1 mEq to about 1.5 mEq per unit dose.

The compositions of the subject invention comprise a pharmaceutically-acceptable carrier preferably comprising a pharmaceutically-acceptable buffer system. Examples of pharmaceutically-acceptable buffer systems useful in the compositions of the subject invention include, but are not limited to, phosphate buffer systems which are a mixture of salts of monohydrogen and dihydrogen phosphate, sodium hydroxide/glycine buffer systems, and carbonate and hydrogen carbonate buffer systems. Preferred buffer systems useful in the compositions of the subject invention are phosphate buffer systems.

A preferred component of the carrier of the compositions of the subject invention is microcrystalline cellulose or a mixture of mycrocrystalline cellulose and carboxymethylcellulose sodium. Microcrystalline cellulose and mixtures of microcrystalline cellulose and carboxymethylcellulose sodium are available from FMC Corporation under the trade name Avicel ®. Such mixtures preferably have a ratio of microcrystalline cellulose to carboxymethylcellulose sodium of from about 20:1 to about 1:1; more preferably from about 15:1 to about 3:1, more preferably still from about 10:1 to about 5:1.

A preferred mixture of microcrystalline cellulose and carboxymethylcellulose sodium is Avicel ® RC591, a commercially available microcrystalline cellulose marketed by FMC Corporation, Food and Pharmaceutical Products Division, Philadelphia, Pa. Avicel ® RC591 is said to be a colloidal form of about 89% microcrystalline cellulose gel blended with about 11% sodium carboxymethylcellulose which is dried; the product is easily dispersed in water. It is insoluble in water, organic solvents and dilute acids. It is partially soluble in dilute alkali. Its chemical and physical specifications are as follows: loss on drying: less than 6% at time of shipment; heavy metals: less than 10 parts per million; viscosity of a 1.2% solution: 65±1%; particle size: less than 0.1% retained on 60 mesh screen, less than 20% retained on a 325 mesh screen. Average particle size is about 28 microns. Its bulk density is about 37 lbs/ft$^3$ loose pack and about 52 lbs/ft$^3$ tight pack. Its specific gravity is 1.55, ash content about 2%, pH of a 2% dispersion in water is 6 to 8. The product is described more fully in FMC Corporation bulletin L-318 "Avicel ® RC-CL Microcrystalline Cellulose" which is incorporated herein by reference.

The quantity of microcrystalline cellulose or mixture of microcrystalline cellulose and carboxymethylcellulose sodium incorporated in the compositions of the subject invention is preferably from about 0.5% to about 3%, more preferably from about 1% to about 2%, more preferably still about 1.5%.

The compositions of the subject invention are intended for peroral administration. Examples of such compositions include preferred liquid compositions, especially aqueous-based liquid compositions, such as syrups, elixirs, suspensions, sprays, and drops. Also preferred are solid compositions which are dissolved or masticated in the mouth such as lozenges, chewable lozenges, powders, and chewable tablets. The pH of such solid dosage forms is determined by dissolving the solid dosage form in artificial saliva at a concentration of 10% of the solid composition and determining the pH of the resulting solution or suspension. (Artificial saliva formulation is disclosed in Fusayema, T., T. Katayori & S. Nomoto, "Artificial Saliva", *Journal of Dental Research*, Vol. 42 (1963), pp. 1183-1197, which is incorporated herein by reference).

Dextromethorphan is relatively insoluble in water at the pH of the compositions of the subject invention. Therefore, it is preferable that sufficient levels of one or more cosolvents be incorporated in the carrier to provide for dissolution of the dextromethorphan in the composition and in the oral cavity. Preferred cosolvents for this purpose include ethanol, propylene glycol, polyethylene glycol, glycerin and sorbitol; more preferred cosolvents include ethanol, propylene glycol and glycerin.

For the liquid compositions of the subject invention, the carrier preferably includes some of the following optional ingredients: water; sweetening agents, such as sucrose, corn syrup, invert sugar, dextrose, sodium saccharin, aspartame, sorbitol, honey, and magnasweet; aromatic ingredients, such as menthol, anethol, camphor, thymol, methyl salicylate, eucalyptus oil and peppermint oil; other flavoring agents; thickening agents, such as carboxymethylcellulose, sodium carboxymethylcellulose, cellulose, glycerine and polyethylene glycol; coloring agents; preservatives, such as sodium benzoate and cetylpyridinium chloride; miscellaneous ingredients, such as potassium sorbate, sodium chloride, titanium dioxide, polysorbate 80, sodium citrate, sodium bicarbonate, sodium hydroxide, aluminum hydroxide and magnesium hydroxide.

In the solid compositions of the subject invention, the carrier preferably includes one or more of the optional ingredients provided hereinabove for the liquid compositions, and additionally the following optional ingredients may be included in such compositions: solid diluents, binders, disintegrants and opacifiers, such as silicon dioxide, talc, povidone, Kaolin, dicalcium phosphate, calcium sulfate, lactose and starch; and miscellaneous ingredients, such as acacia, capsicum, mannitol, sodium alginate, alginic acid, veegum, guar gum, gelatin, ethylcellulose, magnesium stearate, bentonite and sodium lauryl sulfate.

The compositions of the subject invention also may comprise one or more other active drug agents useful for treating coughs and/or colds (cough/cold drug actives). Cough/cold drug actives commonly combined with antitussive agents in commercial products are preferred. Cough/cold drug actives useful in the compositions of the subject invention include antihistamines, bronchodilators, decongestants, expectorants, local anesthetics and anti-inflammatory/analgesics. Preferred examples of such optional drug actives and preferred amounts per unit dose in the compositions of the subject invention include the following: antihistamines, such as chlorpheniramine (preferably from about 1 mg to about 8 mg, more preferably from about 2 mg to about 4 mg) and its salts (e.g., maleate), diphenhydramine (preferably from about 6 mg to about 50 mg, more preferably from about 12 mg to about 25 mg) and its salts (e.g., hydrochloride), brompheniramine (preferably from about 1 mg to about 8 mg, more preferably from about 2 mg to about 4 mg) and its salts, doxylamine (preferably from about 2 mg to about 20 mg, more preferably from about 6 mg to about 12 mg) and its salts (e.g., succinate), triprolidine (preferably from about 0.5 mg to about 4 mg, more preferably from about 1 mg to about 3 mg) and its salts (e.g., hydrochloride); bronchodilators, such as ephedrine (preferably from about 5 mg to about 50 mg, more preferably from about 10 mg to about 25 mg) and its salts (e.9., hydrochloride, sulfate), decongestants, such as pseudoephedrine (preferably from about 10 mg to about 100 mg, more preferably from about 30 mg to about 60 mg) and its salts (e.g., hydrochloride), phenylephrine (preferably from about 2 mg to about 20 mg, more preferably from about 5 mg to about 10 mg) and its salts (e.g., hydrochloride), phenylpropanolamine (preferably from about 5 mg to about 50 mg, more preferably from about 12 mg to about 25 mg) and its salts (e.g., hydrochloride); expectorants, such as guaifenesin (preferably from about 50 mg to about 400 mg, more preferably from about 100 mg to about 200 mg); local anesthetics, such as benzocaine, (preferably from about 1 mg to about 25 mg, more preferably from about 2 mg to about 15 mg), phenol (preferably from about 10 mg to about 150 mg, more preferably from about 20 mg to about 50 mg), dyclonine (preferably from about 1 mg to about 10 mg, more preferably from about 2 mg to about 4 mg) and its salts (e.g., hydrochloride), lidocaine (preferably from about 2 mg to about 20 mg, more preferably from about 4 mg to about 10 mg) and its salts (e.g., hydrochloride), butacaine (preferably from about 5 mg to about 50 mg, more preferably from about 10 mg to about 20 mg) and its salts (e.g. sulfate, hydrochloride), benzyl alcohol (preferably from about 50 mg to about 750 mg, more preferably from about 100 mg to about 500 mg), dibucaine (preferably from about 0.1 mg to about 4 mg, more preferably from about 0.5 mg to about 2 mg) and its salts (e.g., hydrochloride), tetracaine (preferably from about 0.1 mg to about 4 mg, more preferably from about 0.5 mg to about 2 mg) and its salts (e.g., hydrochloride), phenolate sodium (preferably from about 10 mg to about 150 mg, more preferably from about 20 mg to about 50 mg), salicyl alcohol (preferably from about 20 mg to about 200 mg, more preferably from about 50 mg to about 100 mg), hexylresorcinol (preferably from about 1 mg to about 10 mg, more preferably from about 2 mg to about 4 mg), and menthol (preferably from about 2 mg to about 50 mg, more preferably from about 5 mg to about 25 mg); anti-inflammatory/analgesics, such as acetaminophen (preferably from about 60 mg to about 1000 mg, more preferably from about 300 mg to about 650 mg), ibuprofen (preferably from about 100 mg to about 800 mg, more preferably from about 200 mg to about 400 mg) and its salts (e.g., sodium), aspirin (preferably from about 75 mg to about 1000 mg, more preferably from about 300 mg to about 650 mg) and its salts (e.g., sodium), and naproxen (preferably from about 75 mg to about 500 mg, more preferably from about 125 mg to about 300 mg) and its salts (e.g., sodium).

The subject invention also includes methods for treating or preventing cough in humans or lower animals by orally administering a composition disclosed hereinabove. In the methods of the subject invention, the daily dosage of dextromethorphan is preferably from about 0.1 mg/kg to about 10 mg/kg of body weight, more preferably from about 0.5 mg/kg to about 5 mg/kg, more preferably still from about 1 mg/kg to about 3 mg/kg. In the methods of the subject invention, it is preferred that a dextromethorphan composition be orally administered to a patient from about 1 to about 10 times daily, more preferably from about 2 to about 8 times daily, more preferably still from about 3 to about 6 times daily.

EXAMPLES

The following non-limiting examples are provided in order to illustrate the compositions and methods of the subject invention. The liquid and lozenge compositions are made by conventional processes.

EXAMPLE I
Liquid Cough Composition

| Ingredients | Amount/15 ml Dose |
| --- | --- |
| Dextromethorphan HBr | 30.0 mg |
| Propylene Glycol | 1.74 g |
| Ethanol (95%) | 1.5 ml |
| Menthol, Natural | 12.5 mg |
| Eucalyptus Oil | 7.55 mg |
| Flavorants | 0.05 ml |
| Sucrose | 7.65 g |
| Carboxymethylcellulose (CMC) | 7.5 mg |
| Microcrystalline Cellulose and Sodium CMC (Avicel ® RC591, FMC) | 187.5 mg |
| Polysorbate 80 | 3.0 mg |
| Glycerin | 300.0 mg |
| Sorbitol | 300.0 mg |
| F, D & C Red #40 | 3.0 mg |
| Glycine | 28.2 mg |
| Sodium Hydroxide | 7.8 mg |
| Water, Purified | q.s. |

A typical manufacturing process for making the above liquid cough composition is to prepare separate liquid phases by mixing together the following ingredients: (1) dextromethorphan HBr, propylene glycol, ethanol, menthol, eucalyptus oil and flavorants; (2) sucrose, CMC, Avicel, polysorbate 80, glycerin, sorbitol, and part of the water; and (3) colorant, glycine, sodium hydroxide and part of the water. The three liquid phases are then blended together with the remainder of the water to produce the liquid cough composition.

EXAMPLE II
Liquid Cough Composition

| Ingredients | Amount/15 ml Dose |
| --- | --- |
| Dextromethorphan HBr | 15.0 mg |
| Propylene Glycol | 777.0 mg |
| Ethanol (95%) | 1.5 ml |
| Polyethylene Glycol (Carbowax 400) | 750.0 mg |
| Flavorants | 0.05 ml |
| F, D & C Red #40 | 5.1 mg |
| Sodium Phosphate Dibasic | 231.0 mg |
| Sodium Saccharin | 22.5 mg |
| Water, Purified | q.s. |

EXAMPLE III
Liquid Cough Composition

| Ingredients | Amount/15 ml Dose |
| --- | --- |
| Dextromethorphan HBr | 30.0 mg |
| Propylene Glycol | 1.74 g |
| Ethanol (95%) | 1.5 ml |
| Menthol, Natural | 22.5 mg |
| Eucalyptus Oil | 7.5 mg |
| Flavorants | 0.05 ml |
| F, D & C Red #40 | 5.1 mg |
| Sodium Phosphate Dibasic | 231.0 mg |
| Sodium Saccharin | 30.0 mg |
| Sucrose | 8.16 g |
| Glycerine | 750.0 mg |
| Sodium Hydroxide | 3.0 mg |
| Water, Purified | q.s. |

EXAMPLE IV
Liquid Cough Composition

| Ingredients | Amount/15 ml Dose |
| --- | --- |
| Dextromethorphan HBr | 30.0 mg |
| Sucrose | 8.16 g |
| Carboxymethylcellulose (CMC) | 7.5 mg |
| Microcrystalline Cellulose and Sodium CMC (Avicel ® RC591, FMC) | 187.5 mg |
| Polysorbate 80 | 3.0 mg |
| Glycerin | 300.0 mg |
| Sorbitol | 300.0 mg |
| F, D & C Red #40 | 3.0 mg |
| Sodium Phosphate Dibasic | 231.0 mg |
| Sodium Hydroxide | 3.6 mg |
| Sodium Saccharin | 30.0 mg |
| Propylene Glycol | 1.74 g |
| Ethanol (95%) | 1.5 ml |
| Menthol | 22.5 mg |
| Eucalyptus | 7.5 mg |
| Flavorants | 0.05 ml |
| Water, Purified | q.s. |

EXAMPLE V
Liquid Cough Composition

| Ingredients | Amount/15 ml Dose |
| --- | --- |
| Dextromethorphan HBr | 20.0 mg |
| Sucrose | 8.16 g |
| CMC | 7.5 mg |
| Microcrystalline Cellulose and Sodium CMC (Avicel ® RC591, FMC) | 187.5 mg |
| Polysorbate 80 | 3.0 mg |
| Glycerin | 300.0 mg |
| Sorbitol | 300.0 mg |
| F, D & C Red #40 | 3.0 mg |
| Sodium Phosphate Dibasic | 231.0 mg |
| Sodium Hydroxide | 5.0 mg |
| Sodium Saccharin | 30.0 mg |
| Propylene Glycol | 1.74 g |
| Phenol | 100.0 mg |
| Ethanol (95%) | 1.5 ml |
| Menthol | 22.5 mg |
| Eucalyptus Oil | 7.5 mg |

| | |
|---|---|
| Flavorants | 0.05 ml |
| Water, Purified | q.s. |

EXAMPLE VI
Liquid Cough Composition

| Ingredients | Amount/15 ml Dose |
|---|---|
| Dextromethorphan HBr | 30.0 mg |
| Propylene Glycol | 777.0 mg |
| Ethanol (95%) | 1.5 ml |
| Sucrose | 8.16 g |
| CMC | 7.5 mg |
| Microcrystalline Cellulose and Sodium CMC (Avicel ® RC591, FMC) | 187.5 mg |
| Polysorbate 80 | 3.0 mg |
| Glycerin | 300.0 mg |
| Flavorants | 0.05 ml |
| F, D & C Red #40 | 5.1 mg |
| Sodium Phosphate Dibasic | 231.0 mg |
| Sodium Hydroxide | 3.6 mg |
| Sodium Saccharin | 22.5 mg |
| Water, Purified | q.s. |

EXAMPLE VII
Liquid Cough Composition

| Ingredients | Amount/15 ml Dose |
|---|---|
| Dextromethorphan HBr | 30.0 mg |
| Propylene Glycol | 1.74 g |
| Ethanol (95%) | 1.5 ml |
| Menthol, Natural | 22.5 mg |
| Eucalyptus Oil | 7.5 mg |
| Sucrose | 8.16 g |
| CMC | 7.5 mg |
| Microcrystalline Cellulose and Sodium CMC (Avicel ® RC591, FMC) | 187.5 mg |
| Polysorbate 80 | 3.0 mg |
| Flavorants | 0.05 ml |
| F, D & C Red #40 | 5.1 mg |
| Sodium Phosphate Dibasic | 231.0 mg |
| Sodium Saccharin | 30.0 mg |
| Glycerin | 300.0 mg |
| Sodium Hydroxide | 3.6 mg |
| Water, Purified | q.s. |

EXAMPLE VIII
Liquid Cough Composition

| Ingredients | Amount/15 ml Dose |
|---|---|
| Dextromethorphan HBr | 25.0 mg |
| Sucrose | 8.16 g |
| Glycerin | 300.0 mg |
| Sorbitol | 300.0 mg |
| F, D & C Red #40 | 3.0 mg |
| Sodium Phosphate Dibasic | 231.0 mg |
| Sodium Hydroxide | 3.6 mg |
| Sodium Saccharin | 30.0 mg |
| Propylene Glycol | 1.74 g |
| Ethanol (95%) | 1.5 ml |
| Menthol | 22.5 mg |
| Eucalyptus Oil | 7.5 mg |
| Flavorants | 0.05 ml |
| Water, Purified | q.s. |

EXAMPLE IX
Liquid Cough Composition

| Ingredients | Amount/15 ml Dose |
|---|---|
| Dextromethorphan HBr | 30.0 mg |
| Sucrose | 8.16 g |
| Glycerin | 300.0 mg |
| Sorbitol | 300.0 mg |
| F, D & C Red #40 | 3.0 mg |
| Sodium Phosphate Dibasic | 231.0 mg |
| Sodium Hydroxide | 3.6 mg |
| Sodium Saccharin | 30.0 mg |
| Propylene Glycol | 1.74 g |
| Phenol | 100.0 mg |
| Ethanol (95%) | 1.5 ml |
| Menthol | 22.5 mg |
| Eucalyptus Oil | 7.5 mg |
| Flavorants | 0.05 ml |
| Water, Purified | q.s. |

EXAMPLE X
Compressed Tablet Composition

| Ingredients | Amount/2.25 g Lozenge |
|---|---|
| Dextromethorphan Base | 5.0 mg |
| Benzocaine | 1.25 mg |
| Talc | 90.0 mg |
| Flavorants | 15.8 mg |
| Caramel B&C #40 | 69.4 mg |
| Trisodium Phosphate Dodecahydrate | 40.0 mg |
| Magnesium Stearate | 45.0 mg |
| Saccharin | 15.0 mg |
| Emdex | q.s. |

EXAMPLE XI
Liquid Spray Cough Composition

| Ingredients | Amount/3.5 ml Dose |
|---|---|
| Dextromethorphan Base | 25.0 mg |
| Propylene Glycol | 0.7 ml |
| Ethanol (95%) | 1.05 ml |
| Polyethylene Glycol (Carbowax 400) | 0.7 ml |
| Sodium Saccharin | 5.25 mg |
| Flavorants | 0.012 ml |
| F, D & C Red #40 | 1.19 mg |
| Phenol | 75.0 mg |
| Purified Water | q.s. |

EXAMPLE XII
Liquid Spray Cough Composition

| Ingredients | Amount/3.5 ml Dose |
|---|---|
| Dextromethorphan Base | 10.0 mg |
| Propylene Glycol | 0.7 ml |
| Ethanol (95%) | 0.7 ml |
| Polyethylene Glycol (Carbowax 400) | 0.7 ml |
| Monobasic Sodium Phosphate | 8.4 mg |
| Sodium Sacharin | 7.0 mg |
| Flavorants | 0.14 ml |
| F, D & C Red #40 | 1.19 mg |
| Purified Water | q.s. |

The liquid of Example XII is made by adding the dextromethorphan base to the propylene glycol with stirring. The polyethylene glycol, alcohol, flavorants, and sodium saccharin are added incrementally with stirring. The monobasic sodium phosphate is added as a 10% solution in purified water with stirring. The dye is added as a water solution with stirring. Purified water is added to volume with stirring.

While particular embodiments of the subject invention have been described it will be obvious to those skilled in the art that various changes and modifications of the subject invention can be made without departing from the spirit and scope of the invention. It is intended to cover, in the appended claims, all such modifications that are within the scope of this invention.

What is claimed is:

1. An antitussive composition, in dosage unit form, for peroral administration consisting essentially of a safe and effective amount of dextromethorphan and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet, the composition, or 10% artificial saliva solution thereof for solid dosage forms, being at a pH of about 8 to about 11, the carrier comprising a buffer system whereby the composition when mixed with saliva in the mouth is within such pH range.

2. The composition of claim 1 wherein the composition has a basic buffer strength of at least about 0.01 mEq base per dose, and from about 1 mg to about 50 mg dextromethorphan per dose.

3. The composition of claim 2 wherein the composition is at a pH of from about 8.4 to about 10, has a basic buffer strength of from about 0.05 mEq to about 2.5 mEq per dose, and has from about 2.5 mg to about 30 mg dextromethorphan per dose.

4. The composition of claim 2 wherein the composition is an aqueous-based liquid.

5. The composition of claim 3 wherein the composition is an aqueous-based liquid which also comprises from about 0.5% to about 3% Avicel ® RC591.

6. A method of treating or preventing cough in humans by perorally administering to the human a safe and effective amount of a composition of claim any of claims 1-5.

7. The composition of any of claims 2, 3 or 5 wherein the composition is an aqueous-based solution.

8. The composition of any of claims 2, 3 or 5 wherein the composition is a lozenge.

* * * * *